US012559803B1

(12) United States Patent
Liu et al.

(10) Patent No.: US 12,559,803 B1
(45) Date of Patent: Feb. 24, 2026

(54) METHOD FOR DETECTING MOLECULAR CHARACTERISTIC OF GENE-EDITED DISEASE-RESISTANT PIG AND USE THEREOF

(71) Applicant: Institute of Animal Science of Chinese Academy Of Agricultural Sciences, Beijing (CN)

(72) Inventors: Zhiguo Liu, Beijing (CN); Yulian Mu, Beijing (CN); Kui Li, Beijing (CN)

(73) Assignee: INSTITUTE OF ANIMAL SCIENCE OF CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 19/230,110

(22) Filed: Jun. 6, 2025

(30) Foreign Application Priority Data

Dec. 10, 2024 (CN) .......................... 202411808471.5

(51) Int. Cl.
*C12Q 1/6888* (2018.01)
*C12N 15/113* (2010.01)
*C12Q 1/34* (2006.01)
*C12Q 1/6844* (2018.01)

(52) U.S. Cl.
CPC .......... *C12Q 1/6888* (2013.01); *C12N 15/113* (2013.01); *C12Q 1/34* (2013.01); *C12Q 1/6844* (2013.01); *C12N 2310/20* (2017.05); *C12Q 2600/124* (2013.01)

(58) Field of Classification Search
CPC ................................. C12Q 1/68; C07H 21/00
See application file for complete search history.

(56) References Cited

U.S. PATENT DOCUMENTS

2005/0112631 A1* 5/2005 Piepenburg .............. C12Q 1/70
435/6.14
2019/0241954 A1* 8/2019 Doudna ................. C12N 15/11

OTHER PUBLICATIONS

Wang et al. Cas12aVDet: A CRISPR/Cas12a-Based Platform for Rapid and Visual Nucleic Acid Detection. Analytical Chemistry 91:12156-12161 (Year: 2019).*
Janice S. Chen, et al., CRISPR-Cas12a target binding unleashes indiscriminate single-stranded DNase activity, Science, 2018, pp. 436-439, vol. 360.
Kui Xu, et al., CD163 and pAPN double-knockout pigs are resistant to PRRSV and TGEV and exhibit decreased susceptibility to PDCoV while maintaining normal production performance, eLife, 2020, pp. 1-24, vol. 9 No. e57132.

* cited by examiner

*Primary Examiner* — Ethan C Whisenant
(74) *Attorney, Agent, or Firm* — Bayramoglu Law Offices LLC

(57) ABSTRACT

Provided is a method for detecting molecular characteristic of a gene-edited disease-resistant pigs and use thereof. A CRISPR/Cas12a nucleic acid detection system is provided, which includes a nucleic acid detection system 1; the nucleic acid detection system 1 includes crRNA1; and a nucleotide sequence of the crRNA1 is SEQ ID NO: 11. A method for detecting an AE26-CAAS gene-edited disease-resistant pig based on CRISPR/Cas12a system is provided, which has high sensitivity, strong specificity, is simple and easy to use, is convenient for rapid on-site detection, and is economical, simple, efficient and fast, thereby laying the foundation for the commercial production of a gene-edited disease-resistant pig.

10 Claims, 6 Drawing Sheets

Specification includes a Sequence Listing.

| AE26-CAAS gene-edited homozygote pig sample | AE26-CAAS gene-edited heterozygote pig sample | Wild pig sample | Other gene-edited pig sample |

T line –
C line –

AE26-CAAS gene-
edited homozygote
pig sample

AE26-CAAS gene-
edited heterozygote
pig sample

Wild pig sample

Other gene-deited
pig sample

SEQUENCE LISTING

Sequence total quantity: 35
SEQ ID NO: 1               moltype = DNA   length = 27
FEATURE                    Location/Qualifiers
source                     1..27
                           mol_type = other DNA
                           organism = synthetic construct
SEQUENCE: 1
ttctacattt ccaaggccct gggcggc                                          27

SEQ ID NO: 2               moltype = DNA   length = 25
FEATURE                    Location/Qualifiers
source                     1..25
                           mol_type = other DNA
                           organism = synthetic construct
SEQUENCE: 2
tttccaaggc cctgggcggc cgtgg                                            25

SEQ ID NO: 3               moltype = DNA   length = 24
FEATURE                    Location/Qualifiers
source                     1..24
                           mol_type = other DNA
                           organism = synthetic construct
SEQUENCE: 3
ttccaaggcc ctgggcatcc tggg                                             24

SEQ ID NO: 4               moltype = DNA   length = 65
FEATURE                    Location/Qualifiers
source                     1..65
                           mol_type = other DNA
                           organism = synthetic construct
SEQUENCE: 4
taatacgact cactataggg taatttctac taagtgtaga ttacatttcc aaggccctgg      60
gcggc                                                                  65

SEQ ID NO: 5               moltype = DNA   length = 62
FEATURE                    Location/Qualifiers
source                     1..62
                           mol_type = other DNA
                           organism = synthetic construct
SEQUENCE: 5
taatacgact cactataggg taatttctac taagtgtaga tcaaggccct gggcggccgt      60
gg                                                                     62

SEQ ID NO: 6               moltype = DNA   length = 61
FEATURE                    Location/Qualifiers
source                     1..61
                           mol_type = other DNA
                           organism = synthetic construct
SEQUENCE: 6
taatacgact cactataggg taatttctac taagtgtaga taaggccctg ggcatcctgg      60
g                                                                      61

SEQ ID NO: 7               moltype = DNA   length = 65
FEATURE                    Location/Qualifiers
source                     1..65
                           mol_type = other DNA
                           organism = synthetic construct
SEQUENCE: 7
gccgcccagg gccttggaaa tgtaatctac acttagtaga aattaccctatatagtgagtcg      60
tatta                                                                  65

SEQ ID NO: 8               moltype = DNA   length = 62
FEATURE                    Location/Qualifiers
source                     1..62
                           mol_type = other DNA
                           organism = synthetic construct
SEQUENCE: 8
ccacggccgc ccagggcctt gatctacact tagtagaaat taccctatag tgagtcgtat      60
ta                                                                     62

SEQ ID NO: 9               moltype = DNA   length = 61
FEATURE                    Location/Qualifiers
source                     1..61
                           mol_type = other DNA
                           organism = synthetic construct
SEQUENCE: 9
cccaggatgc ccagggcctt atctacactt agtagaaatt accctatagt gagtcgtatt      60
a                                                                      61

-continued

```
SEQ ID NO: 10                moltype = RNA  length = 45
FEATURE                      Location/Qualifiers
source                       1..45
                             mol_type = other RNA
                             organism = synthetic construct
SEQUENCE: 10
taatttctac taagtgtaga ttacatttcc aaggccctgg gcggc                         45

SEQ ID NO: 11                moltype = RNA  length = 42
FEATURE                      Location/Qualifiers
source                       1..42
                             mol_type = other RNA
                             organism = synthetic construct
SEQUENCE: 11
taatttctac taagtgtaga tcaaggccct gggcggccgt gg                            42

SEQ ID NO: 12                moltype = RNA  length = 41
FEATURE                      Location/Qualifiers
source                       1..41
                             mol_type = other RNA
                             organism = synthetic construct
SEQUENCE: 12
taatttctac taagtgtaga taaggccctg ggcatcctgg g                            41

SEQ ID NO: 13                moltype = DNA  length = 25
FEATURE                      Location/Qualifiers
source                       1..25
                             mol_type = other DNA
                             organism = synthetic construct
SEQUENCE: 13
cctcaccatg gccaagggat tctac                                              25

SEQ ID NO: 14                moltype = DNA  length = 25
FEATURE                      Location/Qualifiers
source                       1..25
                             mol_type = other DNA
                             organism = synthetic construct
SEQUENCE: 14
acgatgcttt tgcccttgaa gatgt                                              25

SEQ ID NO: 15                moltype = DNA  length = 15
FEATURE                      Location/Qualifiers
source                       1..15
                             mol_type = other DNA
                             organism = synthetic construct
SEQUENCE: 15
ttttttttatt ttttt                                                        15

SEQ ID NO: 16                moltype = DNA  length = 961
FEATURE                      Location/Qualifiers
source                       1..961
                             mol_type = other DNA
                             organism = synthetic construct
SEQUENCE: 16
tttcacctcc cacctcttgc tcctgggacg tccttcgacc ctcctggatc taacctcagt        60
cttcctgctc ctgtgcctgt tgtcatagct cacagctcac agggagatcc aagccacctg       120
gccgctccct ctcccgctg g ggccagctgc ctgccacctg cccttcagcc cttggtgggc      180
tcccaggctc ctgcagcctg taaccagacc ctgtttgctc ccagcaggca ccctgagcc       240
gcactccgca cgctgttcct gaatctcccc tccagaaccg gagcagtgtc tctacccagt       300
tcagtgacct tcgtctgtct gagccctggt taattttgc ccagtctgca ggctgtgggg       360
ctcctcccct tcagggatat aagcctggtc cgaagctgcc ctgtccctg cccgtcctga        420
gcctccccga gctcccttct caccctcacc atggccaagg gattctacat ttccaaggcc       480
ctgggcggcc gtggccacca tcatcgctct gtctgtggtg tacgcccagg agaagaacaa       540
gaatgccgag catgtccccc aggccccac gtcgcccacc atcaccacca cagccgccat       600
caccttggac cagagcaagc cgtggaaccg gtaccgccta cccacaacgc tgttgcctga       660
ttcctacaac gtgacgctga gaccctacct cactcccaac gcggatggcc tgtacatctt       720
caagggcaaa agcatcgtcc gcttcatctg ccaggagccc accgatgtca tcatcatcca       780
tagcaagaag ctcaactaca ccacccaggg gcacatggtg gtcctgcggg gcgtggggga      840
ctcccaggtc ccagagatcg acaggactga gctggtagag ctcactgagt acctggtggt       900
ccacctcaag ggctcgctgc agcccggcca catgtacgag atggagagtg aattccaggg       960
g                                                                       961

SEQ ID NO: 17                moltype = DNA  length = 987
FEATURE                      Location/Qualifiers
source                       1..987
                             mol_type = other DNA
                             organism = synthetic construct
SEQUENCE: 17
```

```
tttcacctcc cacctcttgc tccttgggacg tccttcgacc ctcctggatc taacctcagt   60
cttcctgctc ctgtgcctgt tgtcatagct cacagctcac agggagatcc aagccacctg   120
gccgctccct ctccccgctg ggccagctgc ctgccacctg cccttcagcc cttggtgggc   180
tcccaggctc ctgcagcctg taaccagacc ctgtttgctc ccagcaggca cccctgagcc   240
gcactccgca cgctgttcct gaatctcccc tccagaaccg gagcagtgtc tctacccagt   300
tcagtgacct tcgtctgtct gagccctggt taattttttgc ccagtctgca ggctgtgggg   360
ctcctcccct tcagggatat aagcctggtc cgaagctgcc ctgtcccctg cccgtcctga   420
gcctccccga gctcccttct caccctcacc atggccaagg gattctacat ttccaaggcc   480
ctgggcatcc tgggcatcct cctcggcctg gcggccgtgg ccaccatcat cgctctgtct   540
gtggtgtacg cccaggagaa gaacaagaat gccgagcatg tcccccaggc ccccacgtcg   600
cccaccatca ccaccacagc cgccatcacc ttgaccaga gcaagccgtg gaaccggtac   660
cgcctaccca caacgctgtt gcctgattcc tacaacgtga cgctgagacc ctacctcact   720
cccaacgcgg atggcctgta catcttcaag ggcaaaagca tcgtccgctt catctgccag   780
gagcccaccg atgtcatcat catccatagc aagaagctca actacaccac ccaggggcac   840
atggtggtcc tgcggggcgt gggggactcc caggtcccag agatcgacag gactgagctg   900
gtagagctca ctgagtacct ggtggtccac ctcaagggct cgctgcagcc cggccacatg   960
tacgagatgg agagtgaatt ccagggg                                        987
```

```
SEQ ID NO: 18          moltype = DNA   length = 23
FEATURE                Location/Qualifiers
source                 1..23
                       mol_type = other DNA
                       organism = synthetic construct
SEQUENCE: 18
tacccagttc agtgaccttc gtc                                          23

SEQ ID NO: 19          moltype = DNA   length = 22
FEATURE                Location/Qualifiers
source                 1..22
                       mol_type = other DNA
                       organism = synthetic construct
SEQUENCE: 19
tgctcggcat tcttgttctt ct                                           22

SEQ ID NO: 20          moltype = DNA   length = 18
FEATURE                Location/Qualifiers
source                 1..18
                       mol_type = other DNA
                       organism = synthetic construct
SEQUENCE: 20
tttcacctcc cacctctt                                                18

SEQ ID NO: 21          moltype = DNA   length = 18
FEATURE                Location/Qualifiers
source                 1..18
                       mol_type = other DNA
                       organism = synthetic construct
SEQUENCE: 21
cccctggaat tcactctc                                                18

SEQ ID NO: 22          moltype = DNA   length = 20
FEATURE                Location/Qualifiers
source                 1..20
                       mol_type = other DNA
                       organism = synthetic construct
SEQUENCE: 22
taatacgact cactataggg                                              20

SEQ ID NO: 23          moltype = DNA   length = 21
FEATURE                Location/Qualifiers
source                 1..21
                       mol_type = other DNA
                       organism = synthetic construct
SEQUENCE: 23
taatttctac taagtgtaga t                                            21

SEQ ID NO: 24          moltype = DNA   length = 24
FEATURE                Location/Qualifiers
source                 1..24
                       mol_type = other DNA
                       organism = synthetic construct
SEQUENCE: 24
cctcaccatg gccaagggat tcta                                         24

SEQ ID NO: 25          moltype = DNA   length = 26
FEATURE                Location/Qualifiers
source                 1..26
                       mol_type = other DNA
                       organism = synthetic construct
```

-continued

```
SEQUENCE: 25
gacgatgctt ttgcccttga agatgt                                            26

SEQ ID NO: 26            moltype = DNA   length = 29
FEATURE                  Location/Qualifiers
source                   1..29
                         mol_type = other DNA
                         organism = synthetic construct
SEQUENCE: 26
cctcaccatg gccaagggat tctacattt                                         29

SEQ ID NO: 27            moltype = DNA   length = 29
FEATURE                  Location/Qualifiers
source                   1..29
                         mol_type = other DNA
                         organism = synthetic construct
SEQUENCE: 27
gcggacgatg cttttgccct tgaagatgt                                         29

SEQ ID NO: 28            moltype = DNA   length = 27
FEATURE                  Location/Qualifiers
source                   1..27
                         mol_type = other DNA
                         organism = synthetic construct
SEQUENCE: 28
cctcaccatg gccaagggat tctacat                                           27

SEQ ID NO: 29            moltype = DNA   length = 27
FEATURE                  Location/Qualifiers
source                   1..27
                         mol_type = other DNA
                         organism = synthetic construct
SEQUENCE: 29
ggacgatgct tttgcccttg aagatgt                                           27

SEQ ID NO: 30            moltype = DNA   length = 27
FEATURE                  Location/Qualifiers
source                   1..27
                         mol_type = other DNA
                         organism = synthetic construct
SEQUENCE: 30
tcaccatggc caagggattc tacattt                                           27

SEQ ID NO: 31            moltype = DNA   length = 26
FEATURE                  Location/Qualifiers
source                   1..26
                         mol_type = other DNA
                         organism = synthetic construct
SEQUENCE: 31
ggacgatgct tttgcccttg aagatg                                            26

SEQ ID NO: 32            moltype = DNA   length = 28
FEATURE                  Location/Qualifiers
source                   1..28
                         mol_type = other DNA
                         organism = synthetic construct
SEQUENCE: 32
cctcaccatg gccaagggat tctacatt                                          28

SEQ ID NO: 33            moltype = DNA   length = 28
FEATURE                  Location/Qualifiers
source                   1..28
                         mol_type = other DNA
                         organism = synthetic construct
SEQUENCE: 33
gcggacgatg cttttgccct tgaagatg                                          28

SEQ ID NO: 34            moltype = DNA   length = 59
FEATURE                  Location/Qualifiers
source                   1..59
                         mol_type = other DNA
                         organism = synthetic construct
SEQUENCE: 34
tccaaggccc tgggcatcct gggcatcctc ctcggcgtgg cggccgtggc caccatcat       59

SEQ ID NO: 35            moltype = DNA   length = 33
FEATURE                  Location/Qualifiers
source                   1..33
                         mol_type = other DNA
```

-continued organism = synthetic construct

SEQUENCE: 35
tccaaggccc tgggcggccg tggccaccat cat                                    33

METHOD FOR DETECTING MOLECULAR CHARACTERISTIC OF GENE-EDITED DISEASE-RESISTANT PIG AND USE THEREOF

CROSS REFERENCE TO THE RELATED APPLICATIONS

This application is based upon and claims priority to Chinese Patent Application No. 202411808471.5, filed on Dec. 10, 2024, the entire contents of which are incorporated herein by reference.

SEQUENCE LISTING

The instant application contains a Sequence Listing which has been submitted in XML format via EFS-Web and is hereby incorporated by reference in its entirety. Said XML copy is named KJ0109S-track-one_Sequence_Listing.xml, created on 05/22/2025, and is 34,110 bytes in size.

TECHNICAL FIELD

The present disclosure belongs to a field of biotechnology, and relates to a method for detecting molecular characteristic of a gene-edited disease-resistant pig and use thereof.

BACKGROUND

Gene-edited breeding is one of the future development directions of animal breeding. The United States, Japan and other countries have granted approval for the commercialization of various gene-edited animals such as GalSafe gene-edited pigs, "Madai" Red Sea Bream, "22-seiki fugu" tiger puffer, and PRLR-SLICK gene-edited cattle. The porcine aminopeptidase N (pAPN) protein has been identified as a critical receptor mediating TGEV (transmissible gastroenteritis virus) to enter cells. Knocking out or editing pAPN gene can make pigs completely resistant to TGEV At present, many teams at home and abroad have successfully obtained pAPN gene-edited pigs, and challenge experiments have confirmed that pAPN gene editing can completely resist TGEV infection. AE26-CAAS gene-edited swine line was developed through gene editing technology. After genetic modification, the pAPN gene of the pig had a 26 bp base deletion in the second exon which caused the pAPN gene to terminate translation prematurely and fail to produce functional APN protein, thereby achieving resistance to porcine transmissible gastroenteritis TGEV virus.

Nucleic acid testing of gene-edited animals is a prerequisite for the supervision, management and industrialization of gene-edited animals and their products. Therefore, it is necessary to develop a rapid method for detecting AE26-CAAS gene-edited disease-resistant pigs.

SUMMARY

The technical problem solved by the present disclosure is how to detect an AE26-CAAS gene-edited disease-resistant pig quickly and accurately.

In order to solve the above technical problems, in a first aspect, the present disclosure provides a clustered regularly interspaced short palindromic repeats (CRISPR) RNA (crRNA) group including crRNA1, wherein a nucleotide sequence of a binding target of the crRNA1 is as shown in SEQ ID NO: 2.

The above crRNA group targets pAPN gene.

In the crRNA group described above, the crRNA1 is obtained by in vitro transcription from a transcription template 1; and the transcription template 1 is a product obtained by annealing a single-stranded DNA molecule as shown in SEQ ID NO: 5 and a single-stranded DNA molecule as shown in SEQ ID NO: 8.

In the crRNA group described above, a nucleotide sequence of the crRNA1 is as shown in SEQ ID NO: 11.

In the crRNA group described above, the crRNA further includes crRNA2, and a nucleotide sequence of a binding target of the crRNA2 is as shown in SEQ ID NO: 3.

In the crRNA group described above, the crRNA2 is obtained by in vitro transcription from a transcription template 2; and the transcription template 2 is a product obtained by annealing a single-stranded DNA molecule as shown in SEQ ID NO: 6 and a single-stranded DNA molecule as shown in SEQ ID NO: 9.

In the crRNA group described above, a nucleotide sequence of the crRNA2 is as shown in SEQ ID NO: 12.

In a second aspect, the present disclosure provides a product, which includes the crRNA1 described in the first aspect, a Cas12a protein, a primer pair for specifically amplifying each binding target, and a single-stranded DNA probe;

or, the product includes the crRNA1 and the crRNA2 described in the first aspect, a Cas12a protein, a primer pair for specifically amplifying each binding target, and a single-stranded DNA probe;

and/or, both two ends of the single-stranded DNA probe are respectively labeled with different groups;

and/or, the group is a fluorophore, a quenching group and/or biotin.

The single-stranded DNA probe is a single-stranded DNA rich in AT bases with a length of 10-50 nt.

The above-mentioned single-stranded DNA probe can be specifically as follows:

a single-stranded DNA probe used for fluorescence detection, which is labeled with a fluorophore and a quenching group at both two ends respectively;

a single-stranded DNA probe used for test strip detection, which is labeled with a fluorophore and biotin at both two ends respectively.

In the product described above, the primer pair consists of a single-stranded DNA molecule as shown in SEQ ID NO: 13 and a single-stranded DNA molecule as shown in SEQ ID NO: 14;

The product described above is a kit, a test strip or a fluorescence detection system.

The product has any of the following functions:

B1) identifying or assisting in identifying an AE26-CAAS gene-edited pig;

B2) identifying or assisting in identifying whether a sample to be tested contains an AE26-CAAS gene editing sequence;

B3) identifying or assisting in identifying a genotype of an AE26-CAAS gene-edited pig.

In a third aspect, the present disclosure provides any of the following substances:

A1) the Cas12a protein and the crRNA described in the second aspect, or a complex formed by the Cas12a protein and the crRNA;

A2) the Cas12a protein, the crRNA1 and the crRNA2 described in the second aspect, or a complex group formed by the crRNA1 and the Cas12a protein or by the crRNA2 and the Cas12a protein;

A2) the primer pair described in the second aspect.

In a fourth aspect, the present disclosure provides a use of the crRNA described in the first aspect and the product described in the second aspect in any of the following:

B1) identifying or assisting in identifying an AE26-CAAS gene-edited pig;

B2) identifying or assisting in identifying whether a sample to be tested contains an AE26-CAAS gene editing sequence;

B3) identifying or assisting in identifying a genotype of an AE26-CAAS gene-edited pig;

B4) preparing a product for identifying or assisting in identifying an AE26-CAAS gene-edited pig;

B5) preparing a product for identifying or assisting in identifying whether a sample to be tested contains an AE26-CAAS gene editing sequence;

B6) preparing a product for identifying or assisting in identifying a genotype of an AE26-CAAS gene-edited pig.

In a fifth aspect, the present disclosure provides a method for identifying or assisting in identifying an AE26-CAAS gene-edited pig, which includes following steps:

C1) performing recombinase polymerase amplification (RPA) using a nucleic acid of a sample to be tested as a template and the primer pair to obtain an RPA amplification product;

C2) preparing a CRISPR-Cas12a detection system including the following components: the RPA product, the Cas12a protein described in the second aspect, the crRNA1 in the crRNA described in the second aspect, and the single-stranded DNA probe described in the second aspect;

C3) reacting the CRISPR-Cas12a detection system and detecting the reaction product, thereby identifying or assisting in identifying the AE26-CAAS gene-edited pig;

In an embodiment of the present disclosure, in the above, detecting the reaction product, thereby identifying or assisting in identifying the AE26-CAAS gene-edited pig is E or F as follows:

E. detecting the fluorescence intensity of each reaction product using a fluorescence detection instrument such as a microplate reader or a fluorescence quantitative PCR instrument:

wherein if the fluorescence intensity of the reaction product of the detection system is extremely significantly (P<0.01) higher than that of the reaction product of the negative control system, then the sample to be tested is derived from or is candidate to be derived from the AE26-CAAS gene-edited pig; if the fluorescence intensity of the reaction product of the detection system 1 is not significantly (P>0.05) higher than that of the reaction product of the negative control system, then the sample to be tested is not derived from or is candidate to be not derived from the AE26-CAAS gene-edited pig; and the negative control system is different from the detection system only in that crRNA1 is not added;

F. detecting each reaction product using a colloidal gold test strip (Cas12/13 special nucleic acid colloidal gold test strip (JY0301), Beijing Libo Taiye Technology Co., Ltd.):

wherein if the reaction product of the detection system detects that both the T line and C line are colored or only the T line is colored (positive), then the sample to be tested is derived from or is candidate to be derived from the AE26-CAAS gene-edited pig; if the reaction product of the detection system 1 detects that C line is colored and the T line is not colored (negative), then the sample to be tested is not derived from or is candidate to be not derived from the AE26-CAAS gene-edited pig.

In a sixth aspect, the present disclosure provides a method for identifying or assisting in identifying a genotype of an AE26-CAAS gene-edited pig, which includes the following steps:

D1) performing RPA amplification using a nucleic acid of a sample to be tested as a template and the primer pair described in the second aspect to obtain an RPA amplification product;

D2) preparing a CRISPR-Cas12a detection system 1 and a CRISPR-Cas12a detection system 2 including the following components;

wherein the CRISPR-Cas12a detection system 1 includes the RPA product, the Cas12a protein described in the second aspect, the crRNA1 in the crRNA described in the second aspect, and the single-stranded DNA probe in the second aspect; and the CRISPR-Cas12a detection system 2 includes the RPA product, the Cas12a protein described in the second aspect, the crRNA2 in the crRNA described in the second aspect, and the single-stranded DNA probe in the second aspect;

D3) reacting the CRISPR-Cas12a detection system 1 and the CRISPR-Cas12a detection system 2 separately, detecting reaction products of the two systems, and thereby identifying or assisting in identifying the genotype of the AE26-CAAS gene-edited pig.

In the above, the step of detecting the reaction products of the two systems, thereby identifying or assisting in identifying the genotype of the AE26-CAAS gene-edited pig can be detected by a colloidal gold test strip (Cas12/13 special nucleic acid colloidal gold test strip(JY0301), Beijing Libo Taiye Technology Co., Ltd.), as follows:

if the reaction product of the detection system 1 detects that both the T line and C line are colored or only the T line is colored (positive), and the reaction product of the detection system 2 detects that the C line is colored and the T line is not colored (negative), then the sample to be tested is derived from or is candidate to be derived from the AE26-CAAS gene-edited pig homozygote; and if the reaction product of the detection system 1 detects that both the T line and C line are colored or only the T line is colored (positive), and the reaction product of the detection system 2 detects that both the T line and C line are colored or only the T line is colored (positive), then the sample to be tested is derived from or is candidate to be derived from the AE26-CAAS gene-edited pig heterozygote.

In the above, the sample to be tested is ear or other tissue of the pig to be tested.

The method is for non-disease diagnosis and treatment purposes.

The experiments of the present disclosure have proved that, the present disclosure provides a method for detecting an AE26-CAAS gene-edited disease-resistant pig based on CRISPR/Cas12a system, which has high sensitivity and strong specificity, is simple and easy to use, is convenient for rapid on-site detection, and is economical, simple, efficient and fast, thereby laying the foundation for the commercial production of a gene-edited disease-resistant pig.

DETAILED DESCRIPTION OF THE EMBODIMENTS

Figure 1A:
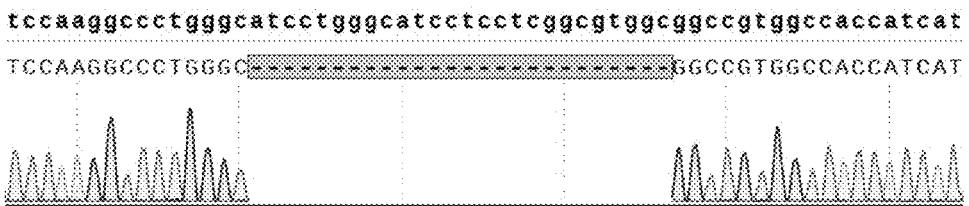
FIGS. 1A-1B show the sequencing results of a standard plasmid for AE26-CAAS gene-edited pig and a standard plasmid for APN gene wild-type pig. In the sequencing result of FIG. 1A, the sequence above is as shown in SEQ ID NO: 34, and the sequence below is as shown in SEQ ID NO: 35. In the sequencing result of FIG. 1B, two sequences are identical, as shown in SEQ ID NO: 34.

The present disclosure is further described in detail below with reference to the examples. The given examples are only for illustrating the present disclosure, but not for limiting the scope of the present disclosure. The following examples are provided as a guide for further improvements by those skilled in the art and are not intended to limit the present disclosure in any way.

The experimental methods in the following examples, unless otherwise specified, are conventional methods and are performed according to the techniques or conditions described in the literature in the art or according to the product instructions.

Unless otherwise specified, the materials and reagents used in the following examples can be obtained from commercial sources.

Unless otherwise specified, the quantitative tests in the following examples were performed three times and the results were averaged.

The present disclosure is described below with reference to the examples. These embodiments are merely examples and are not intended to limit the scope of the present disclosure. Unless otherwise specified, the examples are based on conventional experimental conditions, such as Sambrook J & Russell D W, Molecular Cloning: a Laboratory Manual, 2001, or the conditions recommended by the manufacturer's instructions.

The main reagents used in the following examples are as follows:

LbCas12a protein (EDE0005-2000) was purchased from Guangzhou EDITGENE Technology Co., Ltd.; 10×LbCas12a Cleavage Buffer (EDE0005-B) was purchased from Guangzhou EDITGENE Technology Co., Ltd.; tissue DNA extraction kit (DP304-03) was purchased from Tiangen Biochemical Technology Co., Ltd.; EX Taq enzyme (RR001Q) was purchased from Takara; CloneSmarter TOPO cloning vector kit (C5865-50) was purchased from Taihe Biotechnology (Beijing) Co., Ltd.; *E. coli* DH5a competent cell (B528413-0100) was purchased from Sangon Biotech (Shanghai) Co., Ltd.; primers were synthesized by Beijing Tsingke Biotechnology Co., Ltd.; T7 in vitro transcription kit (AM1354) was produced by Invitrogen; single-stranded DNA fluorescent probe was synthesized by Sangon Biotech (Shanghai) Co., Ltd.; single-stranded DNA colloidal gold test paper probe (EDN-THD02) was purchased from Guangzhou EDITGENE Technology Co., Ltd.; Cas12/13 special nucleic acid detection test strip (JY0301) was purchased from Beijing Libo Taiye Technology Co., Ltd.; TWistAmp Basic kit (TABS03KIT) was purchased from Beijing Libo Taiye Technology Co., Ltd.

The main instruments are as follows: PCR Amplifier (C1000 Touch™, BIO-RAD); high-speed refrigerated centrifuge (Heraeus Multifuge X1R, Thermo); bacterial incubator (MIR-254, SANYO); vortex shaker (SA8, Stuart-equipment); electronic balance (Sartorius SQP, Sartorius Scientific Instrument Co., Ltd.); gel imaging system (BIO-RID, Universal HoodII); constant temperature water bath (HHS-21-4, Changzhou Noki Instrument Co., Ltd.); fluorescence quantitative PCR instrument (QuantStudio™5, Thermo Scientific).

The AE26-CAAS gene-edited pig in the following examples were prepared as follows:

A DKO pig was bred with a wild-type Large White pig (from the Ninghe original breeding farm in Tianjin, hereinafter referred to as a pAPN gene wild-type pig (wide type, WT) to produce offspring pigs, and genotype testing was performed on the offspring pigs, and offspring pigs with only the 26 bp deletion of the pAPN gene, namely AE26-CAAS pig, was selected.

The method of the above genotype detecting is as follows:

The genomic DNA of the ear margin skin or tail skin tissue of the offspring pigs was extracted, and carried out PCR amplification using primers pAPN-PCR-F (5'-TACCCAGTTCAGTGACCTTCGTC-3', SEQ ID NO: 18) and pAPN-PCR-R (5'-TGCTCGGCATTCTTGTTCTTCT-3', SEQ ID NO: 19), and then detected by gel electrophoresis.

Electrophoresis detection showed that the sample with a single band of 260 bp in length was a genotype with pAPN single-gene editing on two homologous chromosomes and a 26 bp deletion, which was named AE26-CAAS gene-edited homozygote pig.

Electrophoresis detection showed that the sample with two bands of 286 bp and 260 bp in length was a genotype with a pAPN single-gene edited on one homologous chromosome and a 26 bp deletion, and the other was a wild-type pAPN gene, which was named AE26-CAAS gene-edited heterozygote pig.

Electrophoresis detection showed that the sample with a single band of 286 bp in length was a wild-type pAPN gene on two homologous chromosomes, which was named pAPN gene wild-type pig or wild-type pig.

Compared with the pAPN gene wild-type pig, in the AE26-CAAS gene-edited homozygote pig, only the 82-107th position of the second exon (82-107th position of the nucleotide sequence of the pAPN gene shown in genbank number NM_214277) of the pAPN gene (genbank number: NM_214277, submitted on 2024 Jun. 2) in two homologous chromosomes are deleted (26 bp bases), and other genes remain unchanged.

Compared with the pAPN gene wild-type pig, in the AE26-CAAS gene-edited heterozygous pig, only the 82-107th position of the second exon (82-107th position of the nucleotide sequence of the pAPN gene shown in genbank number NM_214277) of the pAPN gene (genbank number: NM_214277, submitted on 2024 Jun. 2) in one homologous chromosomes were deleted (26 bp bases), and other genes remain unchanged; the other homologous chromosome is the same as that of the pAPN gene wild-type pig.

The above-mentioned DKO pig was gene-edited pig in which both CD163 and pAPN genes were knocked out simultaneously, and the pAPN gene had two genotypes: 5 bp deletion and 26 bp deletion. After genetic modification, the pAPN gene had a 26 bp base deletion in the second exon, which caused the pAPN gene to terminate translation prematurely and could not generate functional APN protein, thereby achieving resistance to transmissible gastroenteritis of swine virus (TGEV).

DKO pigs are described in the following literature, and they are named double-gene-knockout (DKO) pigs. The literature is Xu K, Zhou Y, Mu Y, Liu Z, Hou S, Xiong Y, Fang L, Ge C, Wei Y, Zhang X, Xu C, Che J, Fan Z, Xiang G, Guo J, Shang H, Li H, Xiao S, Li J, Li K. CD163 and pAPN double-knockout pigs are resistant to PRRSV and TGEV and exhibit decreased susceptibility to PDCoV while maintaining normal production performance. Elife. 2020 Sep. 2; 9:e57132. doi: 10.7554/eLife.57132.

Example 1: RPA-CRISPR/Cas12a Nucleic Acid Detection System for Detecting an AE26-CAAS Gene-Edited Pig I. Acquisition of crRNA 1. Standard Plasmid Construction A tissue DNA extraction kit was used to extract the ear tissue DNA of the AE26-CAAS gene-edited homozygote pig and the wild-type pig (WT) with the pAPN gene, and the upstream and downstream sequences of the target site of the second exon of the pAPN gene were amplified using the primers as shown in Table 1 below to obtain PCR products.

8

TABLE 1

| Primers for amplifying the pAPN gene | | |
|---|---|---|
| Name | Sequence (5'-3') | Length |
| pAPN-F | TTTCACCTCCCACCTCTT (SEQ ID NO: 20) | 18 bp |
| pAPN-R | CCCCTGGAATTCACTCTC (SEQ ID NO: 21) | 18 bp |

The PCR reaction system is as shown in Table 2:

TABLE 2

| PCR reaction system | |
|---|---|
| Component | Volume |
| DNA sample of pig ear tissue | 2.0 µL |
| pAPN-F primer | 0.5 µL |
| pAPN-R primer | 0.5 µL |
| EX Taq | 10.0 µL |
| ddH₂O | 7.0 µL |
| Total volume | 20.0 µL |

PCR reaction program: pre-denaturing at 95° C. for 5 min; denaturing at 95° C. for 30 s, annealing at 65° C. for 30 s, extending at 72° C. for 1 min, 36 cycles; 72° C. for 5 min.

The PCR products were gel-recovered and purified, and the purified products were ligated to the pClone-EZ-TOPO vector (Taihe Biotechnology (Beijing) Co., Ltd., C5865-50). After sequencing verification, the standard plasmid pClone-EZ-TOPO-AE26 for pAPN gene of the gene-edited pig and the standard plasmid pClone-EZ-TOPO-WT for pAPN gene of the wild-type pig were obtained.

pClone-EZ-TOPO-AE26 is a vector obtained by replacing the TOPO I site of the pClone-EZ-TOPO vector with the AE26-CAAS gene editing sequence (SEQ ID NO: 16).

pClone-EZ-TOPO-WT is a vector obtained by replacing the TOPO I site of the pClone-EZ-TOPO vector with a wild-type sequence (SEQ ID NO: 17).

Compared with the wild-type sequence, the above gene editing sequence is a sequence obtained by deleting positions 487-512 of the wild-type sequence.

Figure 1B:
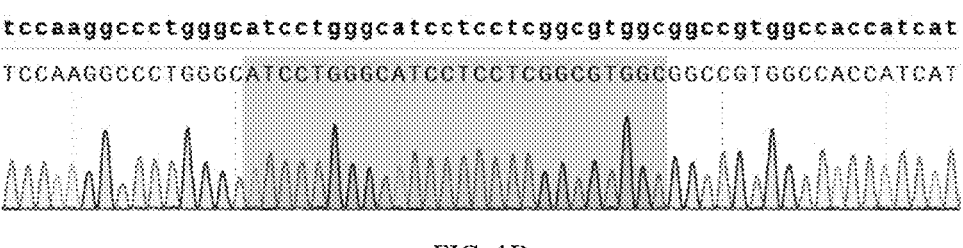

The sequencing results of the two plasmids are shown in FIGS. 1A-1B. FIG. 1A is the sequencing result of the standard plasmid for pAPN gene of the AE26-CAAS gene-edited pig, and FIG. 1B is the sequencing result of the standard plasmid for pAPN gene of the wild-type pig.

2. crRNA Target Design

According to the DNA sequences within 40 bp upstream and downstream of the target site of the second exon of the pAPN gene of the AE26-CAAS gene-edited pig and the wild-type pig, the sequences that met the recognition requirements of LbCas12a were searched, and then three candidate target sites were screened out according to the rules of sequence GC content, sequence complementarity, etc. Among them, AE26crRNA-T1 to AE26crRNA-T2 were candidate target sites screened for gene-edited disease-resistant pigs AE26-CAAS, and WTcrRNA-T1 was a candidate target site screened for pAPN gene wild-type pigs (wildtype, WT), as shown in Table 3.

TABLE 3 crRNA of candidate target sites

| Name | Sequence (5'-3') | Length |
|---|---|---|
| AE26crRNA-T1 (SEQ ID NO: 1) | TTCTACATTTCCAAGGCCCTGGGCGGC | 27 bp |
| AE26crRNA-T2 (SEQ ID NO: 2) | TTTCCAAGGCCCTGGGCGGCCGTGG | 25 bp |
| WTcrRNA-T1 (SEQ ID NO: 3) | TTCCAAGGCCCTGGGCATCCTGGG | 24 bp |

3. Preparation of In Vitro Transcription Template of Specific crRNA

According to the candidate target site sequence, the T7 promoter sequence (TAATACGACTCACTATAGGG, SEQ ID NO: 22) (Chen J S et al. Science, 2018, 360(6387): 436-439.) and the crRNA repeat region template sequence (TAATTTCTACTAAGTGTAGAT, SEQ ID NO: 23) were added to form the forward-strand DNA sequence (SEQ ID NOS: 4-6) as shown in Table 4 of the in vitro transcription template of specific crRNA, and the reverse-strand DNA sequence (SEQ ID NOS: 7-9) was formed according to complementary pairing of the forward-strand DNA sequence.

TABLE 4

Forward-strand and reverse-strand of in vitro transcription template of specific crRNA

| Name | Sequence (5'-3') | Length |
|---|---|---|
| AE26crRNA-T7-F1 (SEQ ID NO: 4) | TAATACGACTCACTATAGGGTAA TTTCTACTAAGTGTAGATTACAT TTCCAAGGCCCTGGGCGGC | 65 bp |
| AE26crRNA-T7-F2 (SEQ ID NO: 5) | TAATACGACTCACTATAGGGTAA TTTCTACTAAGTGTAGATCAAGG CCCTGGGCGGCCGTGG | 62 bp |
| WTcrRNA-T7-F1 (SEQ ID NO: 6) | TAATACGACTCACTATAGGGTAA TTTCTACTAAGTGTAGATAAGGC CCTGGGCATCCTGGG | 61 bp |
| AE26crRNA-T7-R1 (SEQ ID NO: 7) | GCCGCCCAGGGCCTTGGAAATGT AATCTACACTTAGTAGAAATTAC CCTATAGTGAGTCGTATTA | 65 bp |
| AE26crRNA-T7-R2 (SEQ ID NO: 8) | CCACGGCCGCCCAGGGCCTTGAT CTACACTTAGTAGAAATTACCCT ATAGTGAGTCGTATTA | 62 bp |
| WTcrRNA-T7-R1 (SEQ ID NO: 9) | CCCAGGATGCCCAGGGCCTTATC TACACTTAGTAGAAATTACCCTA TAGTGAGTCGTATTA | 61 bp |

The forward and reverse DNA single-strands were synthesized, and the in vitro transcription template of specific crRNA was prepared by annealing. The annealing reaction system in Table 5 was prepared in a PCR tube as follows:

TABLE 5

Annealing reaction system

| Component | Volume |
|---|---|
| Forward-strand DNA (100 µM) | 2.0 µL |
| Reverse-strand DNA (100 µM) | 2.0 µL |
| ddH₂O | 16.0 µL |
| Total volume | 20.0 µL |

The PCR tube was placed in a PCR Amplifier and incubated at 95° C. for 10 min, and then the PCR Amplifier was immediately turned off to allow the double-stranded DNA to cool slowly at room temperature. After 90 min, the PCR tube was placed on ice and incubated for 5 min. The annealed product was the in vitro transcription template of crRNA and can be used for in vitro transcription of crRNA.

4. In Vitro Transcription of Specific crRNA

The transcription system as shown in Table 6 was prepared in a PCR tube using T7 in vitro transcription kit (AM1354) produced by Invitrogen company:

TABLE 6

In vitro transcription system of specific crRNA

| Component | Volume |
|---|---|
| Nuclease-free water | 16.0 µL |
| NTP buffer Mix | 10.0 µL |
| DNA template | 2.0 µL |
| T7 RNA Polymerase Mix | 2.0 µL |
| Total volume | 30.0 µL |

The transcription system was placed in a 37° C. incubator and incubated overnight. The crRNA was recovered using the RNA Purification Recovery Kit produced by NEB.

The recovered crRNA sequences are shown in Table 7:

TABLE 7 crRNA sequence

| Name | Sequence (5'-3') | Length |
|---|---|---|
| AE26crRNA-F1 (SEQ ID NO: 10) | UAAUUUCUACUAAGUGUAGAUUACAU UUCCAAGGCCCUGGGCGGC | 45 bp |
| AE26crRNA-F2 (SEQ ID NO: 11) | UAAUUUCUACUAAGUGUAGAUCAAGG CCCUGGGCGGCCGUGG | 42 bp |
| WTcrRNA-F1 (SEQ ID NO: 12) | UAAUUUCUACUAAGUGUAGAUAAGGC CCUGGGCAUCCUGGG | 41 bp |

II. Designing and Screening RPA Primers

According to the upstream and downstream sequences of the second exon target site of the porcine pAPN gene, RPA amplification primers were designed. The candidate RPA primer sequences are shown in Table 8:

TABLE 8

RPA amplification primers

| Name | Sequence (5'-3') |
|---|---|
| pAPN-RPA-1F (SEQ ID NO: 24) | CCTCACCATGGCCAAGGGATTCTA |
| pAPN-RPA-1R (SEQ ID NO: 25) | GACGATGCTTTTGCCCTTGAAGATGT |
| pAPN-RPA-2F (SEQ ID NO: 26) | CCTCACCATGGCCAAGGGATTCTACATTT |

TABLE 8-continued

| RPA amplification primers | |
|---|---|
| Name | Sequence (5'-3') |
| pAPN-RPA-2R (SEQ ID NO: 27) | GCGGACGATGCTTTTGCCCTTGAAGATGT |
| pAPN-RPA-3F (SEQ ID NO: 28) | CCTCACCATGGCCAAGGGATTCTACAT |
| pAPN-RPA-3R (SEQ ID NO: 29) | GGACGATGCTTTTGCCCTTGAAGATGT |
| pAPN-RPA-4F (SEQ ID NO: 13) | CCTCACCATGGCCAAGGGATTCTAC |
| pAPN-RPA-4R (SEQ ID NO: 14) | ACGATGCTTTTGCCCTTGAAGATGT |
| pAPN-RPA-5F (SEQ ID NO: 30) | TCACCATGGCCAAGGGATTCTACATTT |
| pAPN-RPA-5R (SEQ ID NO: 31) | GGACGATGCTTTTGCCCTTGAAGATG |
| pAPN-RPA-6F (SEQ ID NO: 32) | CCTCACCATGGCCAAGGGATTCTACATT |
| pAPN-RPA-6R (SEQ ID NO: 33) | GCGGACGATGCTTTTGCCCTTGAAGATG |

The RPA reaction system is as shown in Table 9:

TABLE 9

| RPA reaction system | |
|---|---|
| Component | Volume |
| Buffer | 29.5 μL |
| Upstream primer F | 2.4 μL |
| Downstream primer R | 2.4 μL |
| DNA template | 2.0 μL |
| ddH₂O | 11.2 μL |
| MgOAc | 2.5 μL |
| Total volume | 50.0 μL |

The RPA reaction conditions were as follows:
incubating at 37° C. for 30 min.
$3.2 \times 10^{10}$ copies/μL of the standard plasmid pClone-EZ-TOPO-AE26 for pAPN gene of the AE26-CAAS gene-edited pig was used as a template, RPA amplification was performed using the primer pairs (F and R) shown in Table 8, the system shown in Table 9 and the RPA reaction conditions to obtain RPA amplification products.

Figure 2:
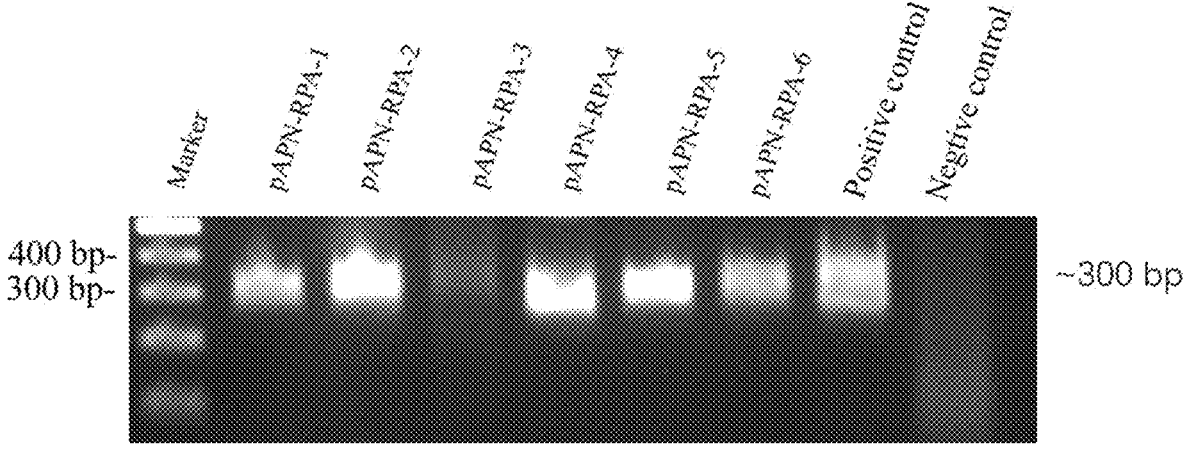
FIG. 2 shows RPA primer amplification results.

The RPA amplification products of each primer pair were subjected to agarose gel electrophoresis. The results are shown in FIG. 2. In the FIG. 2, pAPN-PRA-1 represents pAPN-RPA-1F/pAPN-RPA-1R, and so on. It can be seen that pAPN-RPA-4F/R has a good amplification effect.

Primers pAPN-RPA-4F (SEQ ID NO: 13) and pAPN-RPA-4R (SEQ ID NO: 14) with better amplification effects were selected as the RPA amplification primers.

III. Establishment of RPA-CRISPR/Cas12a Nucleic Acid Detection System and Screening of crRNA The DNA probe in Table 10 is a single-stranded DNA fluorescent probe doubly labeled with a 6-FAM group and a BHQ1 group, and the sequence is 6-FAM-TTATT-BHQ1. The CRISPR/Cas12a fluorescence detection system was prepared according to the components shown in Table 10 below:

TABLE 10

| CRISPR/Cas12a fluorescence detection system | |
|---|---|
| Component | Volume |
| 10 × LbCas12a Cleavage Buffer | 3.0 μL |
| LbCas12a protein (1 μM) | 1.0 μL |
| crRNA (125 nM) | 2.0 μL |
| DNA probe (2 μM) | 6.0 μL |
| Enzyme-free sterile water | 17.0 μL |
| RPA product | 1.0 μL |
| Total volume | 30.0 μL |

Among them, the RPA products were obtained by RPA amplification using standard plasmids pClone-EZ-TOPO-AE26 and pClone-EZ-TOPO-WT as DNA templates. The AE26crRNA-F1, AE26crRNA-F2 and WTcrRNA-F1 detection systems were prepared according to the above system. Three technical replicates were set up for each detection system, and a negative control (NC) without crRNA was set up. The prepared detection system was reacted in a Q5 quantitative PCR instrument at 37° C. for 60 minutes, and the fluorescence intensity was detected every 30 seconds.

Figure 3:
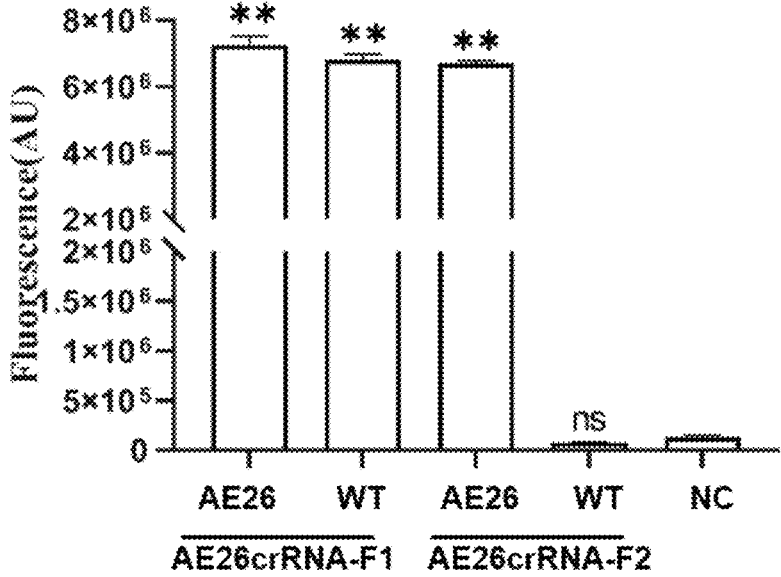
FIG. 3 shows activity detection results of crRNA targeting pAPN gene sequence of the AE26-CAAS gene-edited pig ** indicates an extremely significant difference compared with the negative control group (P<0.01), and ns indicates no significant difference compared with the negative control group (P>0.05).

The results are shown in FIG. 3. AE26crRNA-F1 had a cleavage effect on both the AE26-CAAS sequence and the WT sequence, stimulating trans-cleavage activity, and producing fluorescence with an extremely significant difference ($p < 0.01$) compared with the NC group. It cannot specifically identify the AE26-CAAS sequence, and thus AE26crRNA-F1 could not be used to distinguish AE26-CAAS and WT samples. At the same time, AE26crRNA-F2 only specifically targeted and cut the AE26-CAAS sequence, and produced fluorescence with an extremely significant difference ($p < 0.01$) compared with the NC group, which could specifically identify the AE26-CAAS sequence. Therefore, AE26crRNA-F2 can be used to distinguish AE26-CAAS and WT samples.

Figure 4:
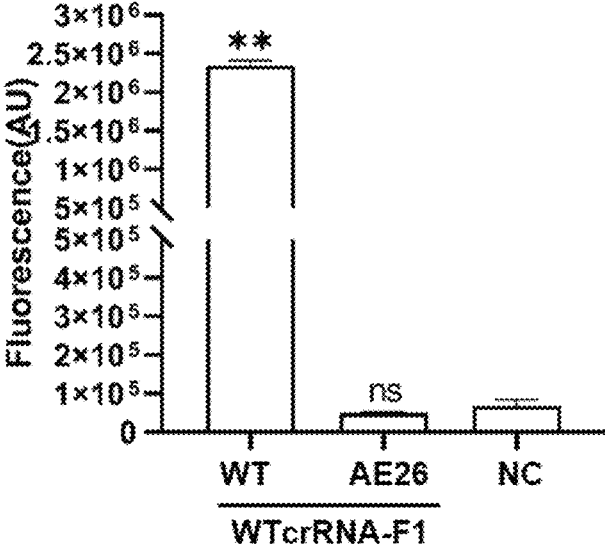
FIG. 4 shows activity detection results of crRNA targeting pAPN gene sequence of the WT pig. ** indicates an extremely significant difference compared with the negative control group (P<0.01), and ns indicates no significant difference compared with the negative control group (P>0.05).

FIG. 4 shows that WTcrRNA-F1 could specifically have a cutting effect on the WT sequence, stimulate trans-cutting activity, and produce fluorescence with an extremely significant difference ($p < 0.01$) compared with the NC group, but could not cut the AE26-CAAS sequence. Therefore, WT crRNA-F1 can specifically recognize the WT sequence and can be used to distinguish AE26-CAAS and WT samples.

IV. Establishment of RPA-CRISPR/Cas12a Nucleic Acid Detection System for AE26-CAAS Gene-Edited Pig 1. RPA Amplification The DNA of the sample to be tested was extracted as a template, and RPA amplification was performed using pAPN-RPA-4F/R primers according to the system shown in Table 9 and RPA reaction conditions to obtain an RPA amplification product.

2. CRISPR/Cas12a Detection of AE26-CAAS Gene-Edited Pig

1) CRISPR/Cas12a Fluorescence Detection

The above RPA amplification product and AE26crRNA-F2 were prepared into a CRISPR/Cas12a fluorescence detection system according to the system shown in Table 10, so as to obtain an AE26crRNA-F2 fluorescence detection system.

The above RPA amplification product and WTcrRNA-F1 were prepared into a CRISPR/Cas12a fluorescence detection system according to the system shown in Table 10, so as to obtain the WTcrRNA-F1 fluorescence detection system.

Three technical replicates were set up for each of the above detection system, and a negative control (NC) without crRNA was set up.

The prepared detection system was reacted in a Q5 quantitative PCR instrument at 37° C. for 60 minutes.

The reaction products of each of the above fluorescence detection systems were used to detect the fluorescence intensity in real time using a Q5 quantitative PCR instrument.

If the fluorescence intensity of the reaction product of the AE26crRNA-F2 detection system is extremely significantly (P value<0.01) higher than that of the reaction product of the negative control system, the sample to be tested contains or is candidate to contain the AE26-CAAS gene editing sequence, or the sample to be tested is derived from or is candidate to be derived from the AE26-CAAS gene-edited pig. If the fluorescence intensity of the reaction product of the AE26crRNA-F2 detection system is not significantly (P>0.05) higher than that of the reaction product of the negative control system, the sample to be tested does not contain or is candidate to not contain the AE26-CAAS gene editing sequence, or the sample to be tested does not derived from or is candidate to be not derived from the AE26-CAAS gene-edited pig.

The above negative control system differed from the AE26crRNA-F2 detection system only in that no crRNA was added.

The above-mentioned AE26-CAAS gene-edited pigs are AE26-CAAS gene-edited homozygote pigs or AE26-CAAS gene-edited heterozygote pigs.

2) CRISPR/Cas12a Test Strip Detection

The above RPA amplification product and AE26crRNA-F2 were prepared into a CRISPR/Cas12a test strip detection system according to the system shown in Table 11, so as to obtain an AE26crRNA-F2 test strip detection system;

The above RPA amplification product and WTcrRNA-F1 were prepared into a CRISPR/Cas12a fluorescence detection system according to the system shown in Table 11, so as to obtain a WTcrRNA-F1 test strip detection system.

The DNA probe in Table 11 is a single-stranded DNA test strip probe doubly labeled with a Biotin group and a 6-FAM group, and the sequence is 6-FAM-TTTTTTTATTTTTTT (SEQ ID NO: 15)-C6Biotin.

TABLE 11

| CRISPR/Cas12a test strip detection system | |
|---|---|
| Component | Volume |
| 10 × LbCas12a Cleavage Buffer | 3.0 μL |
| Cas12a protein (1 μM) | 1.0 μL |
| crRNA (125 nM) | 2.0 μL |
| DNA probe (2 μM) | 6.0 μL |
| Enzyme-free sterile water | 37.0 μL |
| RPA product | 1.0 μL |
| Total volume | 50.0 μL |

The AE26crRNA-F2 and WTcrRNA-F1 test strip detection systems were prepared according to the above system, and a negative control (NC) without crRNA was set up.

Three technical replicates were set up for each of the above detection system, and a negative control (NC) without crRNA was set up.

The prepared detection system was reacted in a PCR Amplifier at 37° C. for 30 minutes, so as to obtain a reaction product (reaction solution).

The reaction products of each of the above-mentioned test strip detection systems were detected using Cas12/Cas13 dedicated nucleic acid test strip.

The conjugated pad end of the test strip was inserted into the reaction solution after opening the tube cover. The liquid level must not exceed the upper end of the conjugated pad, and the area to be interpreted is completely soaked (it takes about 1 to 2 minutes. and the water absorption speed will be reduced and the soaking time of the reading area will be prolonged when the external ambient temperature is low, such as in winter). The test results were read directly according to the color development of the test strip.

If the T line or both the C line and T line of the reaction product of the AE26crRNA-F2 detection system is colored (positive), then the sample to be tested contains or is candidate to contain the AE26-CAAS gene editing sequence, or the sample to be tested is derived from or is candidate to be derived from the AE26-CAAS gene-edited pig. If the C line is colored and the T line of the reaction product of the AE26crRNA-F2 detection system is not colored (negative), then the sample to be tested does not contain or is candidate to not contain the AE26-CAAS gene editing sequence, or the sample to be tested does not derived from or is candidate to not derived from the AE26-CAAS gene-edited pig.

3. CRISPR/Cas12a Detection of AE26-CAAS Gene-Edited Pig's Genotype

The reaction products of each test strip system in 2) of 2 above were detected using a Cas12/13 dedicated nucleic acid detection test strip.

The test results were read directly according to the color development of the test strip.

If the reaction product of the AE26crRNA-F2 detection system is positive (T line or both C line and T line of the product of the AE26crRNA-F2 reaction system is colored), and the reaction product of the WTcrRNA-F1 detection system is negative (C line of the product of the WTcrRNA-F1 reaction system is colored and T line is not colored), then the sample to be tested is derived from or is candidate to be derived from the AE26-CAAS gene-edited homozygote pig.

If the reaction product of the AE26crRNA-F2 detection system is positive (T line or both C line and T line of the product of the AE26crRNA-F2 reaction system is colored), and the reaction product of the WTcrRNA-F1 detection system is also positive (T line or both C line and T line of the product of the WTcrRNA-F1 reaction system is colored), then the sample to be tested is derived from or is candidate to be derived from the AE26-CAAS gene-edited heterozygote pig.

The above-mentioned AE26-CAAS gene-edited pig RPA-CRISPR/Cas12 detection system included: AE26crRNA-F2 and/or WT26crRNA-F1, pAPN-RPA-4F primer, pAPN-RPA-4R primer, LbCas12a protein, and single-stranded DNA probe.

Example 2: Sensitivity Analysis of CRISPR/Cas12a Nucleic Acid Detection System in AE26-CAAS Gene-Edited Pig The standard plasmid pClone-EZ-TOPO-AE26 for pAPN gene of the AE26-CAAS gene-edited pig and the standard plasmid pClone-EZ-TOPO-WT for pAPN gene of the pAPN gene wild-type pig were diluted to the concentration of $3.2 \times 10^{10}$, $3.2 \times 10^{9}$, $3.2 \times 10^{8}$, $3.2 \times 10^{7}$, $3.2 \times 10^{6}$, $3.2 \times 10^{5}$, $3.2 \times 10^{4}$, $3.2 \times 10^{3}$, $3.2 \times 10^{2}$, $3.2 \times 10^{1}$, and $3.2 \times 10^{0}$ copies/μL respectively with nuclease-free ddH$_2$O.

The gradient concentrations of pClone-EZ-TOPO-AE26 plasmid and pClone-EZ-TOPO-WT plasmid were used as templates, RPA amplification was performed using the above mentioned RPA primers (pAPN-RPA-4F/R) and conditions, and the RPA products were detected by electrophoresis.

Figure 5:
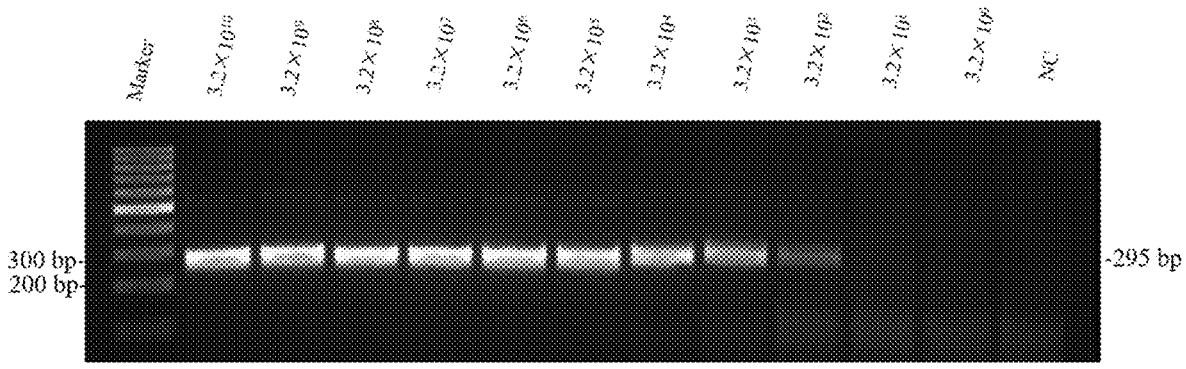
FIG. 5 shows the sensitivity results of RPA amplification targeting pAPN gene sequence of the AE26-CAAS gene-edited pig.

The RPA amplification results of the AE26-CAAS standard plasmid pClone-EZ-TOPO-AE26 plasmid are shown in FIG. 5. The brightness of the electrophoresis band was already quite weak when the plasmid concentration was $3.2 \times 10^2$ copies/μL, and the result was not visible when the plasmid concentration was lower.

Figure 6:
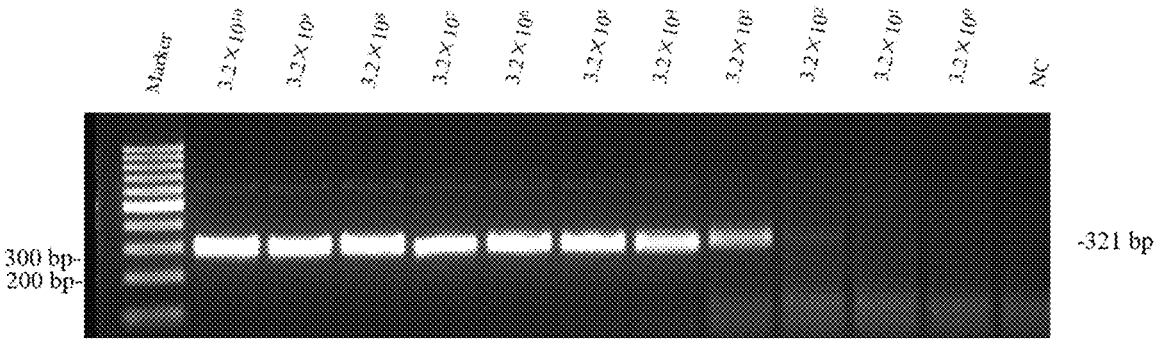
FIG. 6 shows the sensitivity results of RPA amplification targeting pAPN gene sequence of the wild-type (WT) pig.

The RPA amplification results of the WT standard plasmid pClone-EZ-TOPO-WT plasmid are shown in FIG. 6. The brightness of the electrophoresis band was already highly weak when the plasmid concentration was $3.2 \times 10^2$ copies/μL, and the result was not visible when the plasmid concentration was lower.

The above RPA products were used as the detection template, and CRISPR/Cas12a fluorescence detection was performed using the AE26crRNA-F2 fluorescence detection system and the WTcrRNA-F1 fluorescence detection system.

The detection system and reaction conditions are shown in IV of Example 1.

Figure 7:
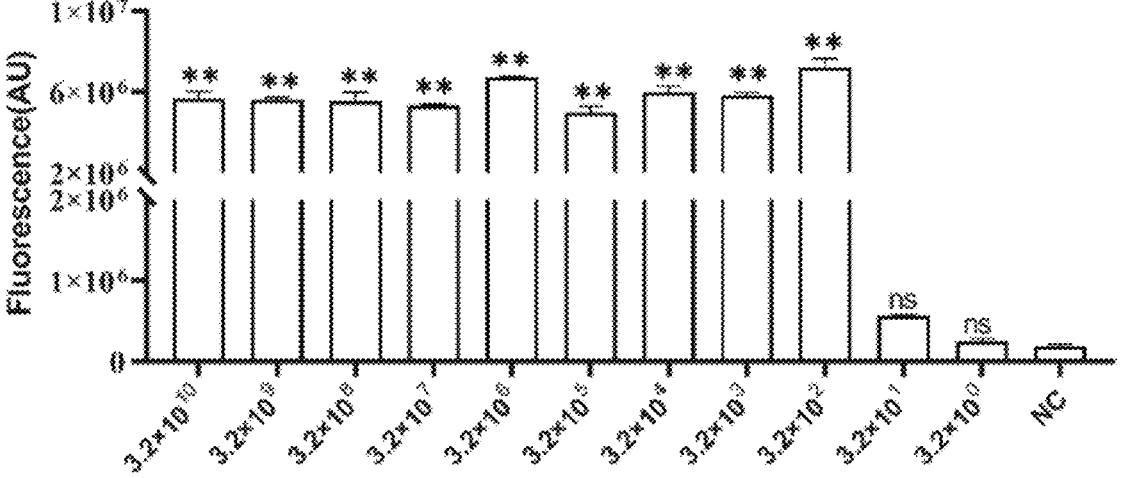
FIG. 7 shows the sensitivity results of fluorescence detection targeting pAPN gene sequence of the pAE26-CAAS gene-edited pig. ** indicates an extremely significant difference compared with the negative control group (P<0.01), and ns indicates no significant difference compared with the negative control group (P>0.05).
Figure 8:
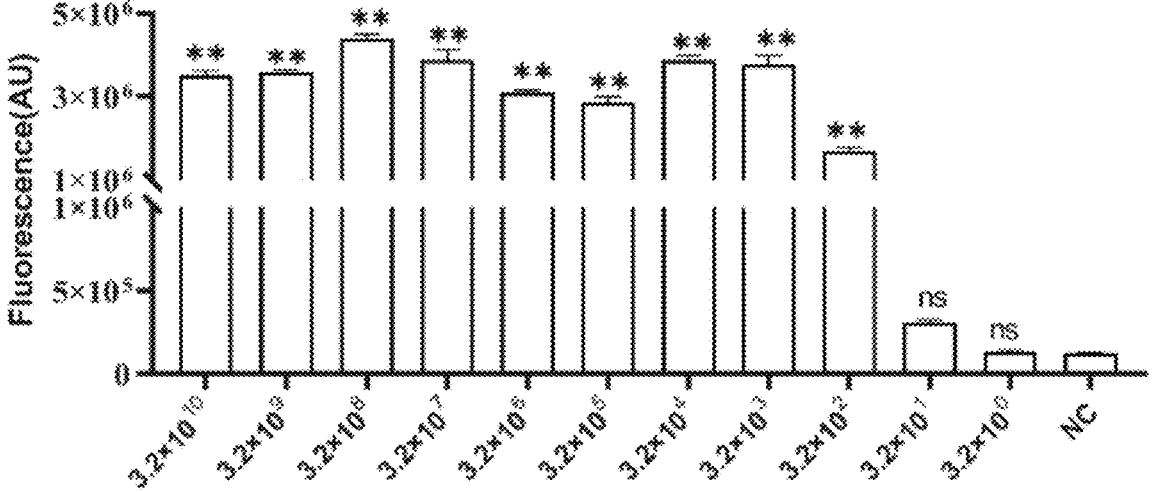
FIG. 8 shows the sensitivity results of fluorescence detection targeting pAPN gene sequence of the wild-type pig. ** indicates an extremely significant difference compared with a negative control group (P<0.01), and ns indicates no significant difference compared with a negative control group (P>0.05).

The fluorescence intensity detection results of the AE26crRNA-F2 fluorescence detection system and the WTcrRNA-F1 fluorescence detection system are shown in FIG. 7 and FIG. 8, respectively. When the standard plasmid concentration was $3.2 \times 10^2$ copies/μL, the detection results were still an order of magnitude different from those of the negative control, and there was an extremely significant difference in fluorescence intensity (P<0.01). The results showed that the detection sensitivity of AE26crRNA-F2 system and WTcrRNA-F1 system was $3.2 \times 10^2$ copies/μL, which was relatively high.

Example 3: Detection of Pig Nucleic Acid Sample Using RPA-Cas12a Nucleic Acid Detection System of AE26-CAAS Gene-Edited Pig The pAPN gene wild-type pig, AE26-CAAS gene-edited pig, and other gene-edited pig (MSTN gene-edited pig) were used to detected by the nucleic acid detection system of AE26-CAAS gene-edited pig provided by the present disclosure, so as to detect whether the system can accurately identify AE26-CAAS gene-edited pig sample.

The above nucleic acid samples were all extracted from the genomic DNA of each pig.

The RPA amplification system was prepared according to the composition in Table 9, and the prepared amplification system was reacted in a thermostat at 37° C. for 30 minutes.

A single-stranded DNA test strip probe double-labeled with Biotin group and 6-FAM group was synthesized, and the sequence was 6-FAM-TTTTTTTATTTTTTT (SEQ ID NO: 15)-C6Biotin. The CRISPR/Cas12a detection system was prepared according to the following components shown in Table 11, and the AE26crRNA-F2 test strip detection system and the WTcrRNA-F1 test strip detection system were prepared according to the above system, and a negative control (NC) without crRNA was set up.

The prepared test strip detection system was reacted in a thermostat at 37° C. for 60 minutes to obtain a reaction product (reaction solution).

The reaction solution was tested with a Cas12/13 dedicated nucleic acid test strip, and the test result was directly read according to the color development of the test strip.

Figure 9:
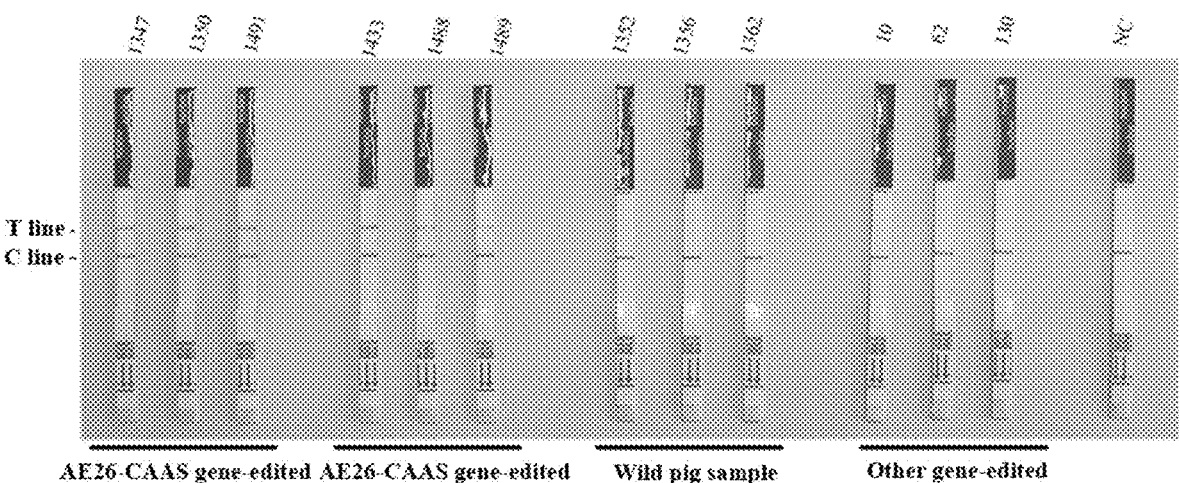
FIG. 9 shows results of detecting pig nucleic acid samples by an AE26crRNA system.
Figure 10:
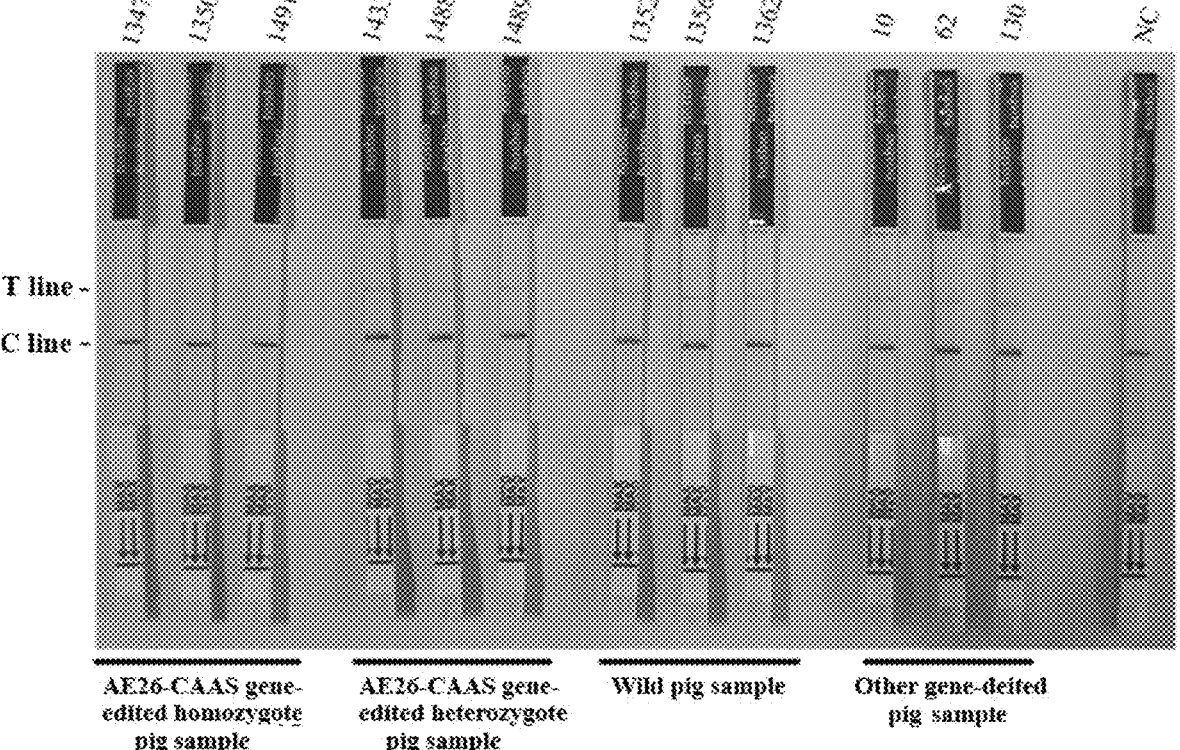
FIG. 10 shows results of detecting pig nucleic acid samples by a WTcrRNA system.

The results are shown in FIG. 9 and FIG. 10. In FIG. 9, the numbers above each test strip indicate the sample ID. When the nucleic acid samples of AE26-CAAS gene-edited homozygote pig, AE26-CAAS gene-edited heterozygote pig, pAPN gene wild-type pig (wild pigs), and other gene-edited pig were detected by the RPA-Cas12a detection system with AE26crRNA-F2 as crRNA, the detection results of nucleic acid samples not containing AE26-CAAS gene editing sequence (nucleic acid samples of wild pig and other gene-edited pig) were consistent with the negative control result, with C line colored and T line not colored, indicating a negative result. The detection results of nucleic acid samples containing AE26-CAAS gene editing sequence (nucleic acid samples of AE26-CAAS gene-edited homozygote pig, AE26-CAAS gene-edited heterozygote pig) showed that both the C line and the T line were colored, indicating a positive result. The results indicated that the AE26crRNA-F2 system combined with colloidal gold test paper can accurately detect nucleic acid samples containing AE26-CAAS gene-edited sequence.

In FIG. 10, when the nucleic acid samples of AE26-CAAS gene-edited homozygote pig, AE26-CAAS gene-edited heterozygote pig, pAPN gene wild-type pig (wild pigs), and other gene-edited pig were detected by the RPA-Cas12a detection system with WTcrRNA-F1 as crRNA, the detection results of nucleic acid samples not containing WT sequence (nucleic acid sample of AE26-CAAS gene-edited homozygote pig) was consistent with the negative control result, with C line colored and T line not colored, indicating a negative result. The detection results of nucleic acid samples containing WT sequence (nucleic acid samples of AE26-CAAS gene-edited heterozygote pig, wild pig and other gene-edited pig) showed that both the C line and the T line were colored, indicating a positive result. The results indicate that the WTcrRNA-F1 system combined with colloidal gold test paper can accurately detect nucleic acid samples containing WT sequence.

Figure 11:
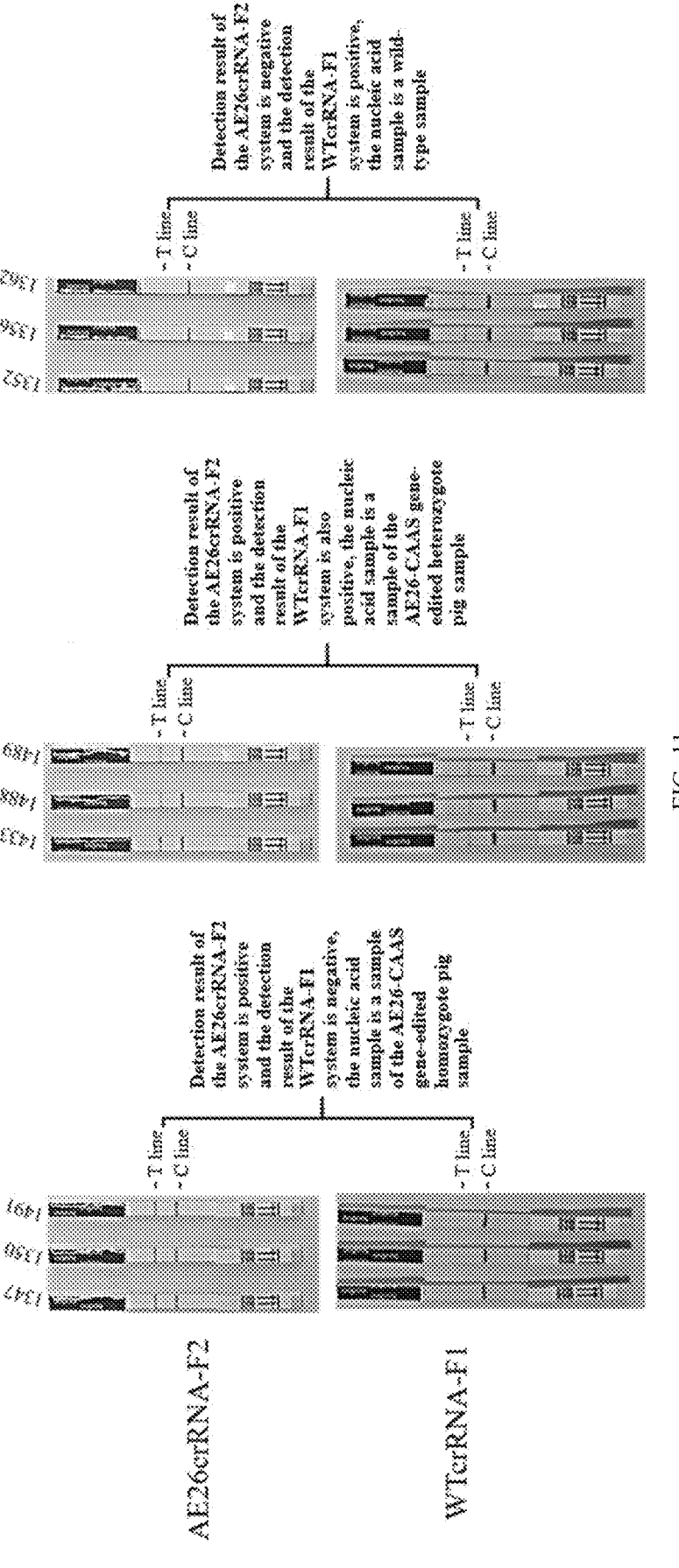
FIG. 11 shows analysis results of detecting pig nucleic acid samples by the combination of an AE26crRNA system and a WTcrRNA system.

The combined use of AE26crRNA-F2 and WTcrRNA-F1 detection systems can accurately determine the genotype of pig nucleic acid samples. As shown in FIG. 11, when the detection result of the AE26crRNA-F2 system is positive and the detection result of the WTcrRNA-F1 system is negative, it indicates that the nucleic acid sample is a sample of the AE26-CAAS gene-edited homozygote pig; when the detection result of the AE26crRNA-F2 system is positive and the detection result of the WTcrRNA-F1 system is also positive, it indicates that the nucleic acid sample is a sample of the AE26-CAAS gene-edited heterozygote pig; and when the detection result of the AE26crRNA-F2 system is negative and the detection result of the WTcrRNA-F1 system is positive, it indicates that the nucleic acid sample is a wild-type sample.

Therefore, by using the crRNAs such as AE26crRNA-F2 and WTcrRNA-F1 and the detection method provided by the present disclosure, the genotype of AE26-CAAS gene-edited pig can be determined quickly, with high sensitivity and high specificity, and can be used to the detection, breeding, production, and supervision of AE26-CAAS gene-edited pig.

The present disclosure has been described in detail above. It is obvious to those skilled in the art that the present disclosure can be implemented in a wider range under equivalent parameters, concentrations and conditions without departing from the spirit and scope of the present disclosure and without unnecessary experiments. While the present disclosure has been described in detail with reference to specific embodiments, it will be appreciated that the invention is capable of further modifications. In short, according to the principles of the present disclosure, the present disclosure is intended to include any changes, uses or improvements to the present disclosure, including changes that depart from the scope disclosed in this application and are made using conventional techniques known in the art. Some essential features may be applied within the scope of the following claims.

What is claimed is:

1. A clustered regularly interspaced short palindromic repeats (CRISPR) RNA (crRNA), comprising crRNA1,
   wherein the nucleotide sequence of a binding target of the crRNA1 is as shown in SEQ ID NO: 2.

2. The crRNA according to claim 1, wherein:
   the crRNA1 is obtained by in vitro transcription from a first transcription template;
   the first transcription template is a product obtained by annealing the single-stranded DNA molecule as shown in SEQ ID NO: 5 and the single-stranded DNA molecule as shown in SEQ ID NO: 8.

3. The crRNA according to claim 1, wherein the nucleotide sequence of the crRNA1 is as shown in SEQ ID NO: 11.

4. The crRNA according to claim 1, further comprising crRNA2,
   wherein the nucleotide sequence of a binding target of the crRNA2 is as shown in SEQ ID NO: 3.

5. The crRNA according to claim 4, wherein:
   the crRNA2 is obtained by in vitro transcription from a second transcription template;
   the second transcription template is a product obtained by annealing the single-stranded DNA molecule as shown in SEQ ID NO: 6 and the single-stranded DNA molecule as shown in SEQ ID NO: 9.

6. The crRNA according to claim 4, wherein the nucleotide sequence of the crRNA2 is as shown in SEQ ID NO: 12.

7. The crRNA according to claim 2, wherein the nucleotide sequence of the crRNA1 is as shown in SEQ ID NO: 11.

8. The crRNA according to claim 2, further comprising crRNA2,
   wherein the nucleotide sequence of a binding target of the crRNA2 is as shown in SEQ ID NO: 3.

9. The crRNA according to claim 3, further comprising crRNA2,
   wherein the nucleotide sequence of a binding target of the crRNA2 is as shown in SEQ ID NO: 3.

10. The crRNA according to claim 5, wherein the nucleotide sequence of the crRNA2 is as shown in SEQ ID NO: 12.

* * * * *